US010918777B2

(12) United States Patent
Neftel et al.

(10) Patent No.: US 10,918,777 B2
(45) Date of Patent: Feb. 16, 2021

(54) DELIVERY SYSTEM AND MODE OF OPERATION THEREOF

(71) Applicant: Debiotech S.A., Lausanne (CH)

(72) Inventors: Frédéric Neftel, Crans-Montana (CH); Pierre Thiebaud, Cressier (CH)

(73) Assignee: Debiotech S.A., Lausanne (CH)

( * ) Notice: Subject to any disclaimer, the term of this patent is extended or adjusted under 35 U.S.C. 154(b) by 325 days.

(21) Appl. No.: 15/517,180

(22) PCT Filed: Oct. 16, 2015

(86) PCT No.: PCT/IB2015/057975
§ 371 (c)(1),
(2) Date: Apr. 6, 2017

(87) PCT Pub. No.: WO2016/059614
PCT Pub. Date: Apr. 21, 2016

(65) Prior Publication Data
US 2017/0368248 A1  Dec. 28, 2017

(30) Foreign Application Priority Data
Oct. 17, 2014 (EP) .................................. 14189455

(51) Int. Cl.
*A61M 1/28* (2006.01)
*G06F 9/30* (2018.01)

(52) U.S. Cl.
CPC ............. *A61M 1/282* (2014.02); *A61M 1/28* (2013.01); *G06F 9/30003* (2013.01); *A61M 2205/12* (2013.01); *A61M 2205/16* (2013.01); *A61M 2205/18* (2013.01); *A61M 2205/3331* (2013.01); *A61M 2205/3334* (2013.01); *A61M 2205/3368* (2013.01)

(58) Field of Classification Search
CPC ................................. A61M 1/28; A61M 1/282
See application file for complete search history.

(56) References Cited

U.S. PATENT DOCUMENTS

| | | | | |
|---|---|---|---|---|
| 5,004,459 | A | * | 4/1991 | Peabody ................. A61M 1/28 604/29 |
| 5,776,345 | A | | 7/1998 | Truitt et al. |
| 9,907,897 | B2 | | 3/2018 | Burbank et al. |
| 2008/0200868 | A1 | * | 8/2008 | Alberti .................... A61M 1/28 604/29 |

(Continued)

FOREIGN PATENT DOCUMENTS

| | | |
|---|---|---|
| CN | 103619372 A | 3/2014 |
| EP | 0471000 B1 | 2/1992 |

(Continued)

OTHER PUBLICATIONS

International Search Report for PCT/IB2015/057975 dated Jun. 29, 2016.

(Continued)

*Primary Examiner* — William R Carpenter
(74) *Attorney, Agent, or Firm* — Andre Roland S.A.; Nikolaus Schibli

(57) ABSTRACT

A medical system suitable for delivering a fluid to a patient according to multiple modes of operation, including a safety mode that additionally enables the delivery or the treatment to continue even when a probable anomaly is detected.

44 Claims, 11 Drawing Sheets

(56) References Cited

U.S. PATENT DOCUMENTS

| | | | |
|---|---|---|---|
| 2010/0191181 A1 | 7/2010 | Childers et al. | |
| 2014/0018727 A1* | 1/2014 | Burbank | A61M 1/1656 604/28 |
| 2014/0073837 A1* | 3/2014 | Kerkhoffs | A61M 1/1086 600/16 |
| 2014/0194809 A1* | 7/2014 | Plahey | A61M 1/282 604/28 |
| 2016/0166748 A1* | 6/2016 | Meyer | A61M 1/1696 210/646 |

FOREIGN PATENT DOCUMENTS

| | | |
|---|---|---|
| EP | 1195171 B1 | 4/2002 |
| EP | 1648536 B1 | 4/2004 |
| JP | 2013-537087 | 9/2013 |
| WO | WO03082144 A2 | 10/2003 |
| WO | WO 2006054720 A1 | 6/2008 |
| WO | WO2010006137 A1 | 1/2010 |
| WO | WO2010088360 A1 | 8/2010 |
| WO | WO2010108955 A1 | 9/2010 |
| WO | WO2012036836 A2 | 3/2012 |

OTHER PUBLICATIONS

Written Opinion of the International Searching Authority for PCT/IB2015/057975 dated Jun. 29, 2016.
Chinese Office Action dated Jan. 17, 2020 for Patent Application 201580067153.0.
Japanese Office Action dated Aug. 21, 2019 for Patent Application 2017-519846.
European Search Opinion dated Jul. 20, 2020 for Application N° EP20159341.5.
European Search Report dated Jul. 20, 2020 for Application N° EP20159341.5.

* cited by examiner

DELIVERY SYSTEM AND MODE OF OPERATION THEREOF

CROSS-REFERENCE TO RELATED APPLICATIONS

The present application is a U.S. national stage application of PCT/M2015/057975 filed on Oct. 16, 2015 designating the United States, and claims foreign priority to European patent application EP 14189455.0, filed on Oct. 17, 2014, the contents of both documents being herewith incorporated by reference in their entirety.

FIELD OF THE INVENTION

The invention relates to a medical system designed to deliver a fluid to a patient according to several modes of operation one of them being a safe mode. Said safe mode also allows the delivery or treatment to continue if a probable anomaly is detected.

PRIOR ART

The device now disclosed may be suited to numerous delivery devices. However, it is particularly well suited to treatments using peritoneal dialysis.

Peritoneal dialysis is a therapeutic means of purifying the blood. It allows a patient suffering from renal insufficiency to eliminate impurities such as urea and excess water which would usually have been eliminated from their body by kidneys functioning normally. This therapeutic means makes use of the patient's peritoneum. The peritoneal membrane has a very large surface area and comprises a great many blood vessels. It thus acts as a natural filter between the blood and any liquid potentially present in the peritoneal cavity. Numerous patents disclose systems for performing peritoneal dialyses (EP 1 648 536 A2, EP 0 471 000 B1, EP 1 195 171 B1, EP 1 648 536 B1 which are incorporated by reference into the present description) for injecting and removing fluid into and from the patient's peritoneum.

Treatment by peritoneal dialysis is relatively simple and comprises at least one cycle of three distinct phases:
- the "fill": the system injects dialysate into the patient's peritoneal cavity (this is also referred to as the injection phase);
- the "dwell": the system leaves the dialysate in the peritoneal cavity for a determined length of time (also referred to as the stasis phase);
- the "drain": the system removes the dialysate present in the peritoneal cavity (this is also referred to as the drainage phase).

In the present document, a phase may be a fill, a dwell or a drain (it being possible for each phase to be complete or partial), a cycle comprises a fill, a dwell and a drain, and the treatment may comprise several cycles. In other words, the phases may be repeated during one and the same treatment.

Systems generally referred to as APD (automated peritoneal dialysis) systems are designed to perform several fill, dwell and drain phases succeeding one another, in other words several cycles succeeding one another during one and the same treatment. This type of system thus performs a treatment over a number of hours. APD systems are also particularly suitable for use over night and/or at the patient's home.

Such systems comprise means designed to check and/or monitor their correct operation. These means may measure or estimate or calculate the volumes injected into or removed from the peritoneum. For example, these means may comprise a sensor connected to a processor. Checking these volumes is of primordial importance. Specifically, under no circumstances must the system inject too great a quantity of dialysate into the peritoneal cavity nor leave a significant volume at the end of the treatment or at the end of each drain phase. That could have several impacts on the patient's health (damage the peritoneum, cause pulmonary edema, loss of ultrafiltration capability, respiratory insufficiency or cardiac insufficiency, etc.) or, at the very least, make the patient rather more uncomfortable even if it does not have vital consequences.

If a sensor is defective and the system fails to detect this defectiveness, the sensor may cause an overestimate or underestimate of the volumes injected and/or removed during the treatment. This error is all the more significant when the treatment comprises several cycles because, in that case, the estimation error is repeated on each cycle and becomes cumulative. This error may be the result of one or more factors, such as wear or a defect (temporary or otherwise) of the machine, of the pumping system, of the sensors, movement on the part of the patient, a change in temperature, etc. If the system comprises a disposable part (tube, cassette, reservoir, etc.) and a reusable part (machine, electronics, sensor), it may also be the result of a poor connection/coupling between the two parts.

In an anomaly, the systems of the prior art simply alert the patient or the medical personnel so that one or more actions can be taken to correct the problem. Certain very far-sighted systems even prefer to alert the user even when a potential anomaly is detected.

If the treatment is being performed overnight and/or in the patient's own home, certain alarms may disturb the patient's sleep without this being truly necessary and/or may needlessly alert the patient when the latter does not have the capability of intervening. In addition, the true cause of the triggering of the alarm may sometimes be the fact that the patient has simply moved during treatment. Thus, it would be needless to awaken the patient like systems of the prior art do, because the fault would be only temporary and would not truly endanger the safety of the patient.

In other circumstances, the anomaly may persist or at least doubt as to the anomaly may lead the system of the prior art to shut down the system prematurely, leading to an interruption to treatment that the patient needs. In general, the systems of the prior art favor interrupting the treatment as soon as there is a malfunction that could carry a risk to the patient. In particular, no system of the prior art foresees modifying the treatment in order to limit this patient risk while at the same time continuing to operate in the presence of such a malfunction.

GENERAL DESCRIPTION OF THE INVENTION

The invention presented in this document introduces greater intelligence into the processing of the data and/or operation of the system so as to optimize the treatment even in the event of an anomaly or in the event of a potential anomaly being detected. In particular, the invention can switch mode of operation (namely for example modify one or more parameters of the treatment) after detecting a possible anomaly and this new mode of operation may be called "safe" because it is potentially less effective than the original mode but allows the patient to be provided with a treatment which is still more favorable then prematurely shutting down the treatment while nevertheless guaranteeing the safety of the patient. The principle of the invention is a system designed to guarantee a minimum treatment (the most favorable to the patient in the given circumstances, for example according to the level of awareness of the status of the system and/or of the surroundings of the patient) while at the same time providing an effect that is favorable to the patient's health.

In other words, the system invented makes it possible to carry out a treatment that is less effective when it detects a defect, which meets less tight specifications (for example duration of treatment, fluid flow rate, etc.) than a system that does not have a defect but which nevertheless guarantees the safety of the patient and the continuity of his/her treatment. Thus, unlike the systems of the prior art, if one or more defects or faults are detected, or suspected, rather than halting the treatment and going into alarm mode (and thus disturbing the patient and giving him or her only an incomplete treatment that is insufficient and potentially harmful), the system invented will adjust the treatment (some or all of the parameters that describe same) to guarantee that the treatment is continued to its end, that the required precision for patient safety is maintained, but without guaranteeing that the specifications of the machines are adhered to.

The system presented in the document is particularly suited to peritoneal dialysis systems and even more particularly suited to automated peritoneal dialysis (APD) systems, because of the repeating of the cycles. Specifically, the addition of a repetitive cycle may have a very strong impact on the imprecision of a device if the latter is faulty, leading to a systematic fault risk. On each cycle, this fault will combine with the fault of the preceding cycle to give rise, after several cycles, to an effect that is highly significant.

A first aspect of the invention relates to a medical device which comprises at least two modes of operation. A first mode of operation referred to as normal in which the system defines a collection of parameters (for example a volume, a delivery rate, a number of cycles, etc.) in order to achieve the desired effect using a certain therapeutic prescription. A second mode of operation referred to as "safe" in which the system has detected a failure or an anomaly or a disrupting event which forces the system to modify at least one of said parameters in order to continue the treatment with a new collection of parameters (for example to decrease or increase the volume, the delivery rate and/or the cycles, etc.). Said mode of safe operation may potentially not reach the same level of effectiveness (which can be measured for example through the quantity of ultrafiltrate, the duration of the treatment, etc.) as the mode of normal operation. However, this mode of operation makes it possible to achieve a minimum treatment effectiveness, which is notably more favorable than interrupting the treatment, while at the same time guaranteeing patient safety.

According to a second aspect of the invention, the device comprises a mode of safe operation, as described previously, but the parameters of which may be adapted according to the significance of the anomaly and/or the way in which it is evolving. In other words, the safe mode is less effective than the normal mode, this mode making it possible to guarantee patients safety while at the same time adapting the parameters so as to provide the patient with treatment that is optimal according to the actual circumstances. For example, it may be that a drift in a sensor has been detected and that as the data from the sensor gradually drift, the device adapts the parameters such as a progressive lowering in the delivery rate or volume of fluid injected or an increase in the volume drained. Depending on the measurements taken by the various sensors, and if the doubt as to the presence of a fault increases or the estimate of the risk of the impact this fault will have on the quality of the treatment or on the risk that the patient is running increases, the mode of safe operation will adapt the treatment parameters each time leading to a lowering of the effectiveness of the treatment but guaranteeing that the new treatment will remain safe for the patient.

In one embodiment, the system comprises at least one sensor (pressure sensor, temperature sensor, delivery rate sensor, etc.) connected to a processor intended to define the status of the system or to monitor a parameter of the treatment or of the environment of the system. The processor may be designed to recognize a failure of this sensor or to assume a failure with this sensor. This can be done either by duplicating the sensors and comparing the values given by the two entities. A difference means that one of the elements at least is faulty. It may also be done by comparing the response of the sensor against an ideal theoretical curve. In the event of a difference that is too pronounced, the sensor will be considered to be faulty. If the fault with this sensor can be neglected, the system may decide to continue with the treatment in a mode of normal operation. If the fault with this sensor leads to consequences that may potentially jeopardize patient safety, then the system has the capability of defining a new collection of parameters according to a mode of safe operation capable of continuing the treatment and guaranteeing patient safety even in the presence of the detected or suspected anomaly.

During treatment, the anomaly may evolve, for example intensify, and the system is then (once again) designed to redefine a new collection of parameters accordingly that will make it possible to guarantee patient safety to the end of the treatment, even if this treatment loses in effectiveness. For example, if a sensor used for calculating, measuring or estimating the volumes injected or drained becomes defective, the system may decrease the quantity injected or increase the quantity drained in order to limit the risks of overfilling the patient that could be the result of such a failure of this sensor. On each cycle and during the various phases, the system may gradually modify one or more parameters: volume displaced, pump delivery rate, temperature, etc.

In one embodiment, the system comprises two sensors ensuring redundancy of the measurement of a parameter ensuring patient safety. These sensors may for example measure (or calculate using the processor) the delivery rate so as to be sure of the precision of the delivery rate of dialysate injected or drained. In the event of a fault with at least one of the two sensors, the safe mode will preferably be activated, thereby ensuring patient safety on the basis of just one functional sensor. The failure of one of the two sensors may be detected from the fact that the discrepancy between the two sensors exceeds a certain threshold or that the pressure profiles are not consistent with one another or with the operation of the pump.

In the foregoing paragraphs the failure described is that of a sensor. It is obvious to a person skilled in the art that it could be any kind of system failure. Such a failure may affect a sensor but may equally affect any other part of the system and be identified by a sensor present in the system.

According to a third aspect of the invention, the device has the ability to decide to maintain treatment (in normal or safe mode) under conditions that are optimum for patient safety or to stop the treatment prematurely depending on the anticipated effectiveness of each of these options (continuing the mode of normal operation, switching to a mode of safe operation, prematurely stopping the treatment). In other words, the system comprises a processor designed to evaluate the potential effect of the alternative treatment or treatments and compare the effect on the health of the patient with the effect of prematurely stopping the treatment. Thus, the system is capable without intervention from the patient or the care personnel, of deciding on the best option for the patient's health and safety under all circumstances. In particular, it may be considered that if the fault is detected at an advanced stage in the treatment, for example when a certain predefined percentage of the treatment has been carried out, it is preferable to stop the treatment rather than continuing under conditions of lower effectiveness.

A fourth aspect of the invention relates to a method of controlling a peritoneal dialysis apparatus comprising the following steps:

observing at least one parameter relating to the treatment determining a first acceptable range of values for said parameter switching from one mode of operation to a first mode of safe operation if the data of said at least one parameter are outside said first acceptable range of values.

The method may involve progressively adapting the acceptable range of values and the mode of safe operation suited to this range of values for said parameter.

LIST OF FIGURES

The invention will be better understood hereinafter by means of a number of illustrated examples.

It goes without saying that the invention is not restricted to these embodiments.

FIGS. 3 to 7 schematically illustrate the possible operation of such a device.

Figure 8:
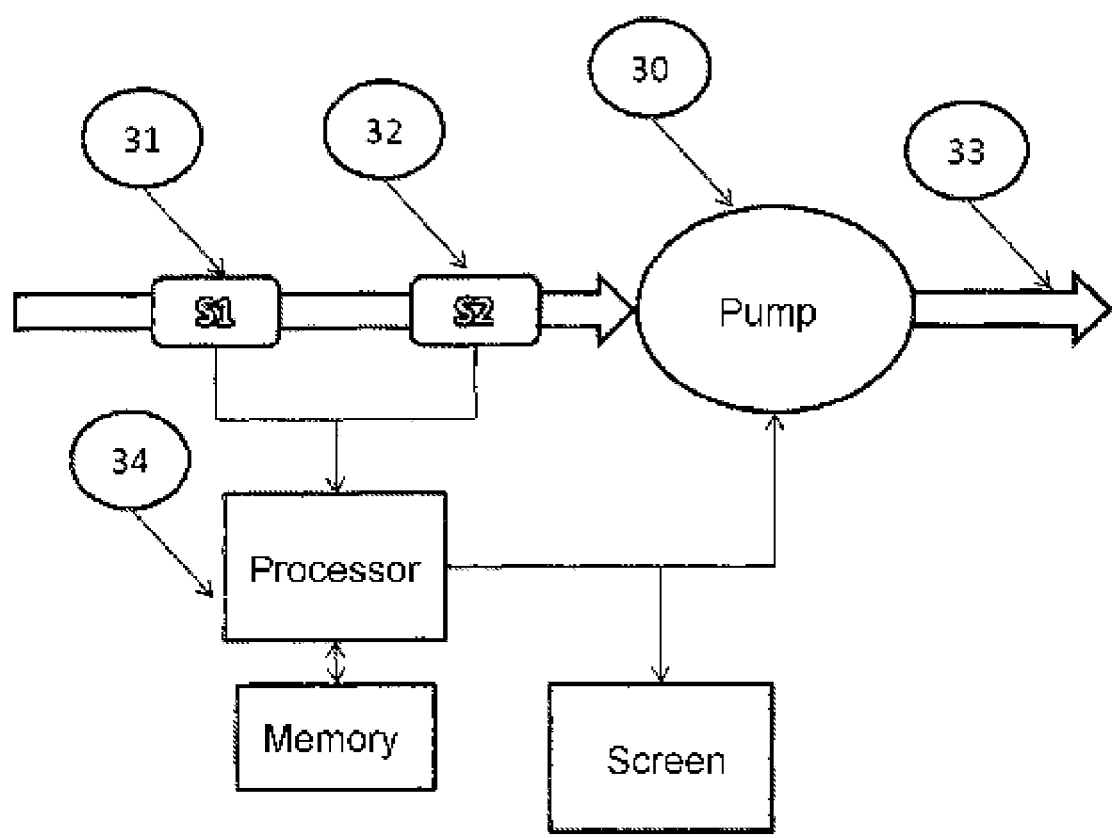

FIG. 8 briefly illustrates a minimum embodiment.

FIGS. 9 to 11b schematically illustrate the possible operation of such a device.

NUMERICAL REFERENCES USED IN THE FIGURES

1 Cycler
2 Cassette
3 Fluid inlet or outlet
4 Actuator (valve)
5 Pressure sensor
6 Region of coupling of the cassette to a pressure sensor
7 Pumping mechanism
8 Actuator (of the pumping mechanism)
9 Valve
10 Sensor
11 Processor
12 Possible mode of operation
20 Parameterizing
21 Pump activation
22 First condition met?
23 Switching the mode of operation
24 Previous parameters unchanged
25 Second condition met?
26 Stop the pump
30 Pumping system
31 Pressure sensor 1
32 Pressure sensor 2
33 Direction of flow of the fluid propelled by the pump
34 Processor

DETAILED DESCRIPTION OF THE INVENTION

In the present document, the detailed description of the invention includes embodiments of devices, systems and methods which are given by way of illustration. Of course, other modes of embodiment are conceivable and may be applied without departing from the scope or spirit of the invention. The detailed description that follows must therefore not be considered to be limiting.

Unless indicated otherwise, the scientific and technical terms used in the present document have the meanings commonly employed by those skilled in the art. The definitions given in this document are mentioned with a view to making the frequently used terms easier to understand and are not intended to restrict the scope of the invention.

The direction indications used in the description and the claims such as "top", "bottom", "left", "right", "upper", "lower" and other directions or orientations are mentioned in order to provide greater clarity with reference to the figures. These indications are not intended to limit the scope of the invention.

Verbs "to have", "to comprise", "to include" or equivalent are used in this document in a broad sense and in general terms signify "include, but not limited to".

The term "or" is generally employed in a broad sense encompassing "and/or" unless the context clearly indicates the opposite.

The term "treatment" is to be understood as meaning the action or series of actions aimed at achieving one or more therapeutic objectives during a defined period of time. Here, a treatment begins from the moment the patient switches the system on (and/or couples the fluidic connections) and continues until the patient switches this system off (and/or disconnects the fluidic connections). The system defines a collection of parameters (pump speed, pressure, actuation, temperature, pressure monitoring, liquid volumes displaced, starting and stopping of phases, etc.) for performing a treatment. A treatment is said to be normal if the collection of parameters makes it possible substantially to achieve the predefined therapeutic objectives. The duration of the treatment is qualified as normal if this duration is substantially close to the normal treatment duration. In other words, the term "normal" here qualifies the operation/progress of the treatment.

The term "effectiveness" is to be understood as qualifying an effect, in this instance a treatment. Also, the term "effective" may be defined as follows: "something that produces the expected effect". In other words, a treatment that is effective needs to be understood to mean a treatment defined by a prescription and which has produced the desired effect (for example quantity of ultrafiltrate obtained at the end of the treatment). Thus, the term "effectiveness" here qualifies the result of the treatment. There is an idea of relativity that comes out of the term "effectiveness". Specifically, a treatment may be more or less effective. This effectiveness may vary considerably from one treatment to another and is dependent on numerous variables. In the present document, the effectiveness between normal treatment and the treatment actually carried out is compared.

The expression "mode of safe operation" is to be understood to mean a mode of operation of the system that does not necessarily make it possible to achieve the predefined objectives or the desired effectiveness of treatment referred to as normal. In other words, the mode of operation referred to as normal operation should in theory be more effective than a mode of safe operation. In the field of medicine, this mode of safe operation must also meet patient safety requirements.

Figure 2:
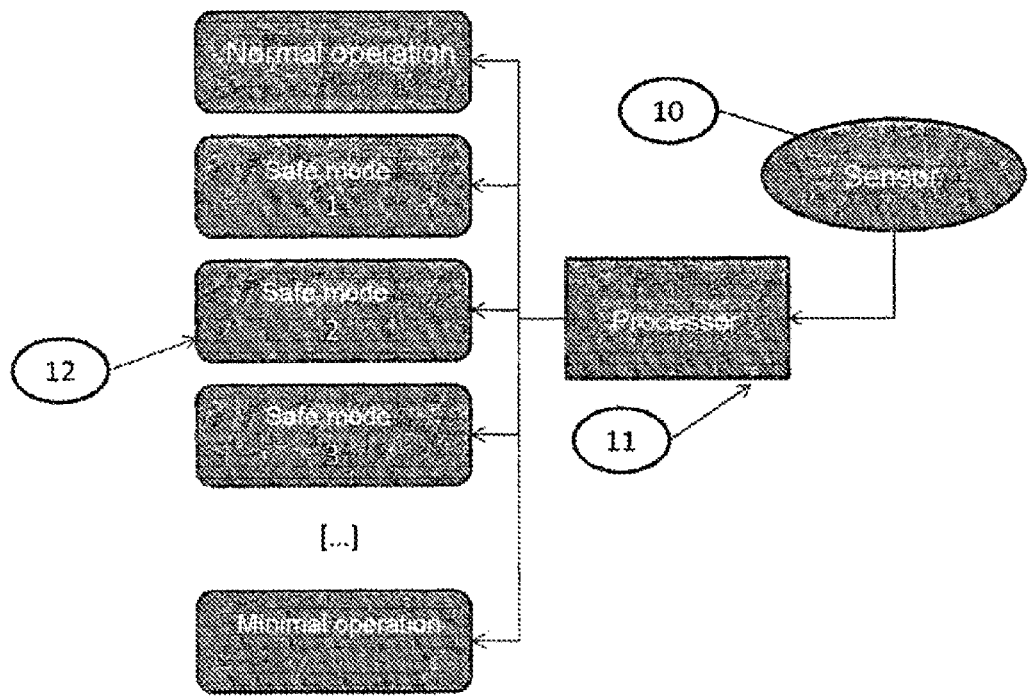
FIG. 2 illustrates various possible modes of operation.

Concept and Methods of Operation:

According to the embodiment of FIG. 2, the system comprises a checking device employing at least one element of the system such as an electronic processor (11) and a sensor (10). The system is designed to determine or select a collection of parameters (volume injected, drained, heating of the fluid, pressure, delivery rate of the pump, duration, number of cycles and phases, etc.) that can be predefined by the care personnel. Using this checking device, the system is designed to define or select at least the following modes: a mode of normal operation and a mode of safe operation. A mode of safe operation may be a mode of minimal operation. There may also be several intermediate modes of safe operation. These modes are characterized by their lower effectiveness as compared with the normal mode while remaining more effective than the minimal safe mode.

A memory connected to the processor may be used to record the various modes of operation and the system is designed by virtue of the checking device to select one of these modes of operation. A doctor may preparameterize one or more different modes of operation according to different possible scenarios (defective sensor, etc.). A decision tree may be used by the checking device to choose the appropriate mode of operation. The selection may also be performed in cascade where the checking device moves on from one mode of operation to another until a mode of operation compatible with the conditions known to the system is obtained.

Figure 3:
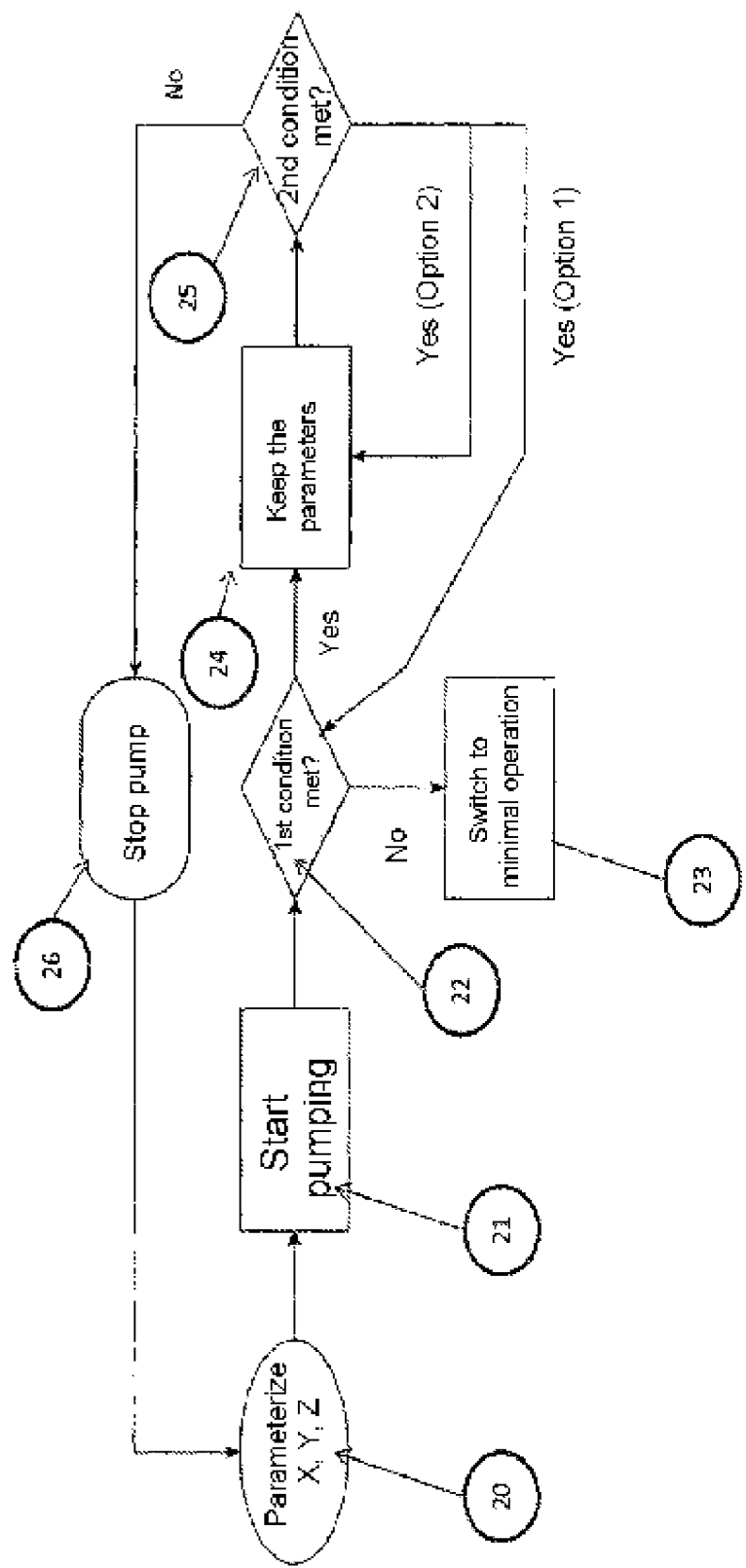

In one embodiment, the system is designed to operate as disclosed in FIG. 3. At the start of treatment, the system defines parameters (20) according to the prescription defined or programmed or given by the care personnel. This first mode of operation will be termed normal. The system starts the pump and, thanks to the sensors, the system verifies or monitors a collection of data. If a first collection of conditions (22) is not met then the system can switch to a mode of safe operation (which may be the minimal mode) guaranteeing patient safety and continuing the treatment even though a condition is not met (for example a sensor is faulty). The treatment will then undoubtedly be less effective but will remain safe and the patient will nevertheless have received some treatment. This is a mode of safe operation. If the first condition is met then the treatment can continue (or begin) with the parameters defined previously. A collection of conditions may include one or more conditions (not crossing a threshold and/or exiting a range of operation and/or range of measurements and/or a data mean and/or a step correctly completed, etc.). The various modes of operation may be characterized by a collection of predefined parameters and the system moves on from one mode of operation to another as soon as one or more operating conditions are not met (a threshold is crossed, a prescribed quantity of fluid is not completely used, a sensor is defective, sensor data are incoherent, there is too great a measurement discrepancy between the various sensors, etc.).

The system may be designed to monitor this first collection of conditions right from the start of treatment and/or during the course of treatment (periodically or otherwise). For example, at each start of phase and/or at regular or random time intervals. A second collection of conditions may be verified right at the start of the treatment and/or during the treatment (periodically or otherwise). If this second collection of conditions (24) is met then the system may be designed to:

periodically reverify the first collection of conditions (option 1), and/or maintain the previously defined mode of operation (option 2).

The system may carry out the check on the various conditions sequentially or in parallel. Such verifications may be performed just once or throughout the treatment at regular or variable time intervals.

When the second condition is not met, the system may decide:

to stop the treatment, or to redefine (20) a new collection of parameters so as to continue the treatment in a mode of safe operation which nevertheless remains less effective (for example longer because the new parameterizing defines a slower delivery rate) than the mode of normal operation but more effective than the mode of minimal operation. Before redefining this new collection of parameters, the system may temporarily stop the pump.

Figure 4:
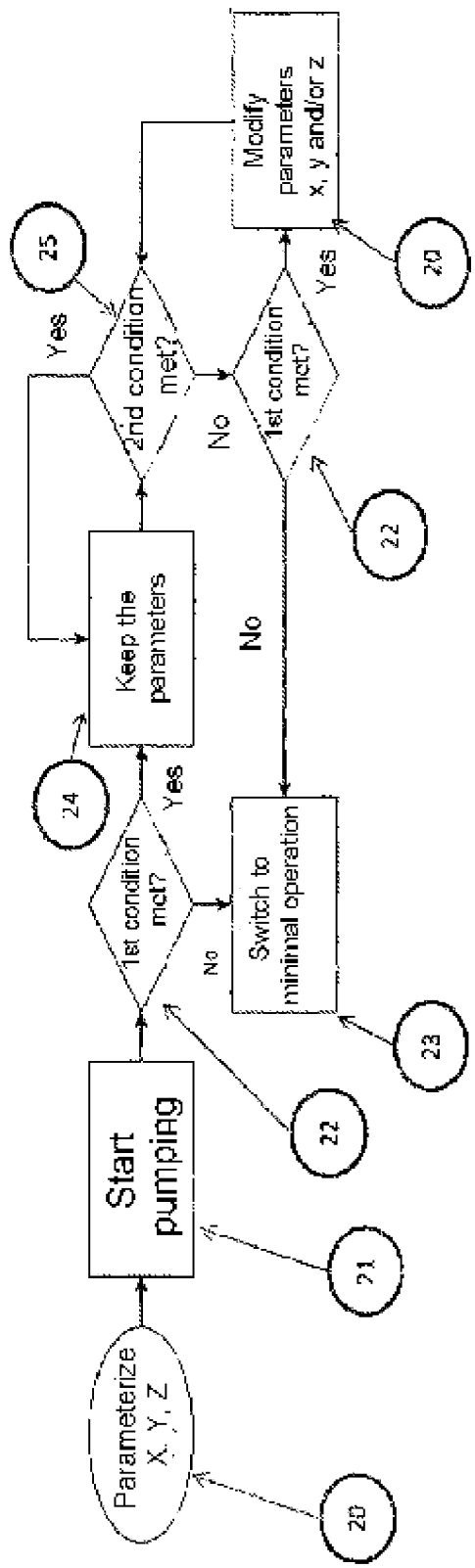

In one embodiment, the system is designed to operate as divulged in FIG. 4. The system at the start of treatment parameterizes a mode of normal operation and the process is performed for the most part as in FIG. 3. As long as the second collection of conditions is met, the system will continue to operate according to the mode of normal operation. If the second collection of conditions is not met, the system will also verify the first collection of conditions. If the first collection of conditions is not met then the system will switch to a mode of minimal operation. If the first collection of conditions is still met then the system will modify one or more parameters and will switch to a mode of safe operation so that the second collection of conditions is met. The second collection of conditions may be adapted according to predefined parameters. Namely, the second collection of conditions may still be identical even in the event of a change of mode of operation, or it may be modified. In the latter instance, one or more conditions may be less restrictive (for example: broadened range: threshold extended, acceptance of a step not correctly completed, etc.). As long as the second collection of conditions is met the system may maintain the parameters defined previously (whether that be in the normal or the safe mode). The system may also be designed to revert to a mode of normal operation after a certain length of time or according to certain conditions. The system will perform a loop check on the conditions and will adjust the mode of operation to best suit, according to the data it receives.

Figure 5:
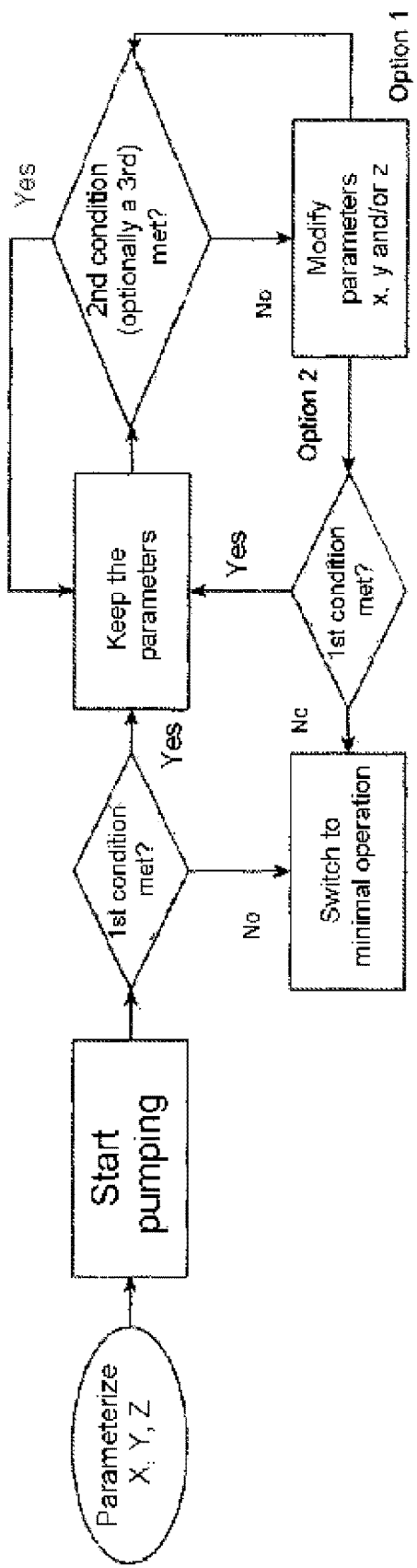

In one embodiment, the system is designed to operate as disclosed in FIG. 5. The system at the start of treatment parameterizes a mode of normal operation and the process takes place in part as in FIGS. 3 and 4. The system verifies a second collection of conditions and optionally a third collection of conditions (at the same time or sequentially or in the event of a change of mode of operation).

Figure 6:
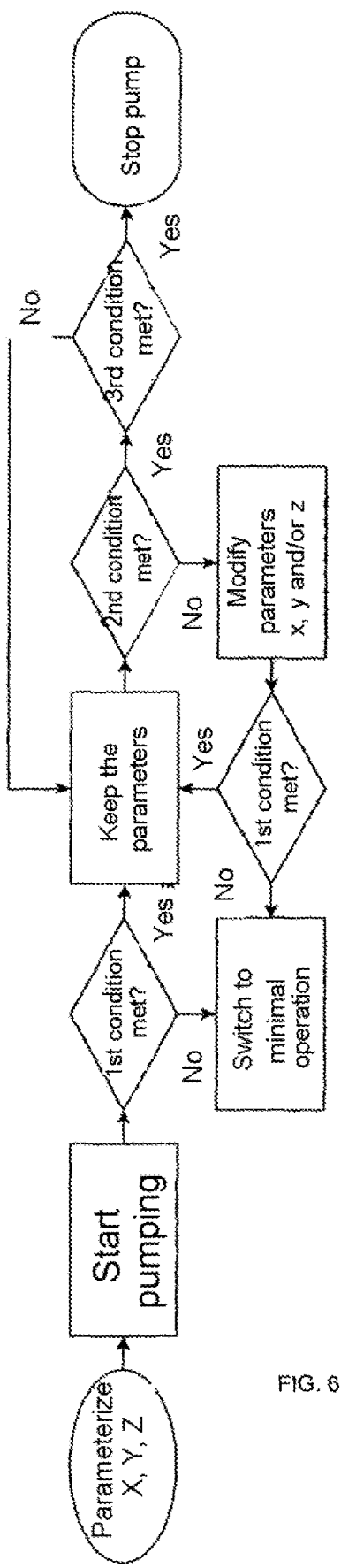
Figure 7:
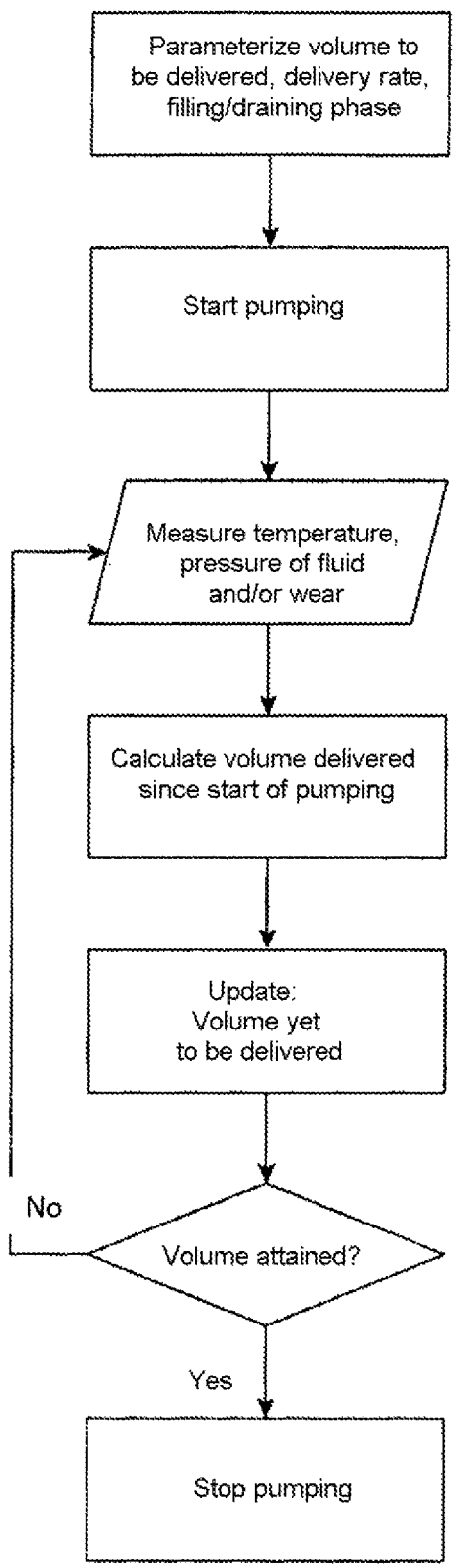

In one embodiment, the system is designed to operate as disclosed in FIG. 6. The system at the start of treatment parameterizes a mode of normal operation and the process takes place in part as in FIGS. 3, 4 and 5. In this system, the third collection of conditions is monitored, insofar as the second collection of conditions is met. However, as long as the third collection of conditions is not met, the treatment continues according to the previous mode of operation. And when the third collection of conditions is met, then the treatment is stopped. Here, the third condition may be the volume injected, the programmed number of cycles, the duration of the treatment.

Figure 9:
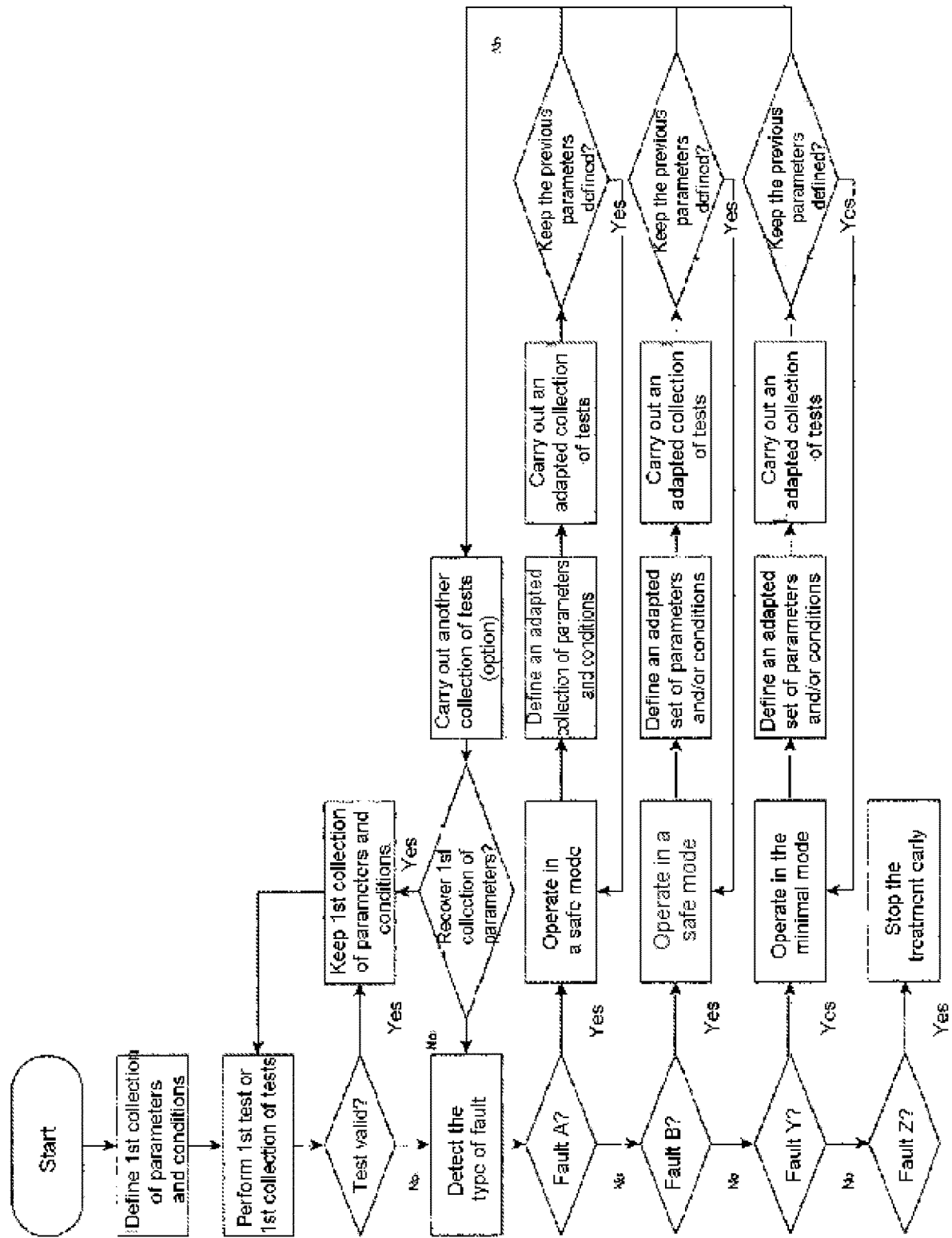

In an embodiment disclosed through FIG. 9, the system comprises a certain number of predefined safe modes of which one is a minimal mode. By predefinition, it may be appreciated that the system already has a certain number of safe modes one of them being a minimal mode in which the parameters are all defined at least before the start of the treatment. A strategy may be defined for determining (using algorithms, a fuzzy-logic approach, or an approach of the artificial intelligence type for example) the new parameters of the safe treatment according to the parameters of the normal treatment and the circumstances encountered. These various parameters will tend towards the series of parameters defining the minimal safe mode. During the course of treatment, the system regularly performs various tests and observes the way in which the various elements of which it is made up behave. These tests may be performed during the treatment or may require a temporary stoppage of the treatment. For preference, these tests are performed by the processor of the system and use data relating to the operation of the system (pressure, temperature, delivery rate, component status, etc.) and/or of the progress of the treatment (start/end of cycle, of phase, remaining quantity of fresh dialysate, quantity removed, UF, etc.). If, during the course of one of these tests or observations, the system notices or suspects a failure or a condition that has not been met, it may decide to implement the mode of safe operation. The mode of safe operation chosen will be dependent on the analysis made by the system of the actual or supposed fault. Once in this safe mode, the system will continue the treatment and the tests and checks. It may be that the switch to a first safe mode renders these tests and checks normal. It is also possible that these tests and checks will remain abnormal but that in such a safe mode the continuation of the treatment will be safe for the patient. If, over the course of time, the results of the tests and checks become poor again or deteriorate excessively, the system may decide to switch to a second mode of safe operation, less effective than the previous modes, but once again safe for the patient. This process may be repeated several times until the minimal safe mode is reached.

In one embodiment, the system may follow a strategy in which each mode of operation is tested in order to obtain satisfactory test results (normal→A→B→C→ . . . →Z). In another embodiment, one mode of safe operation may be favored according to the results of the previous test or tests (normal→A→D→B). Although in these examples mention is made of several modes of safe operation which succeed one another, the system may simply pass on from a mode of normal operation to a suitable mode of safe operation (normal→C). The system may also be designed to revert to a mode of normal operation (B→normal).

At any time, the system may decide to stop the therapy if it considers that the therapy is sufficiently well advanced (according to a series of criteria defined in advance) or if it considers that even the minimal safe mode is unable to guarantee patient safety.

Figure 10:
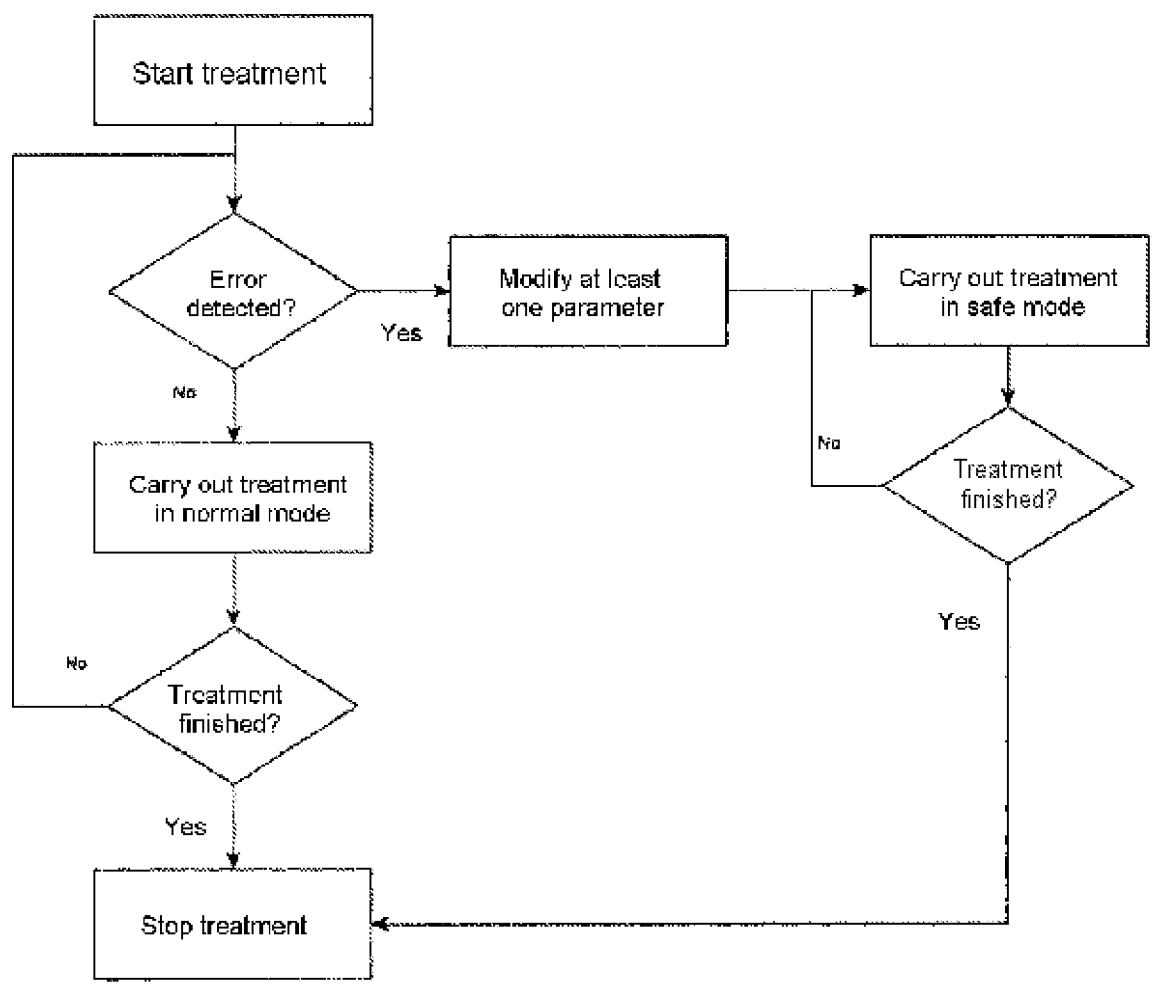
Figure 11A:
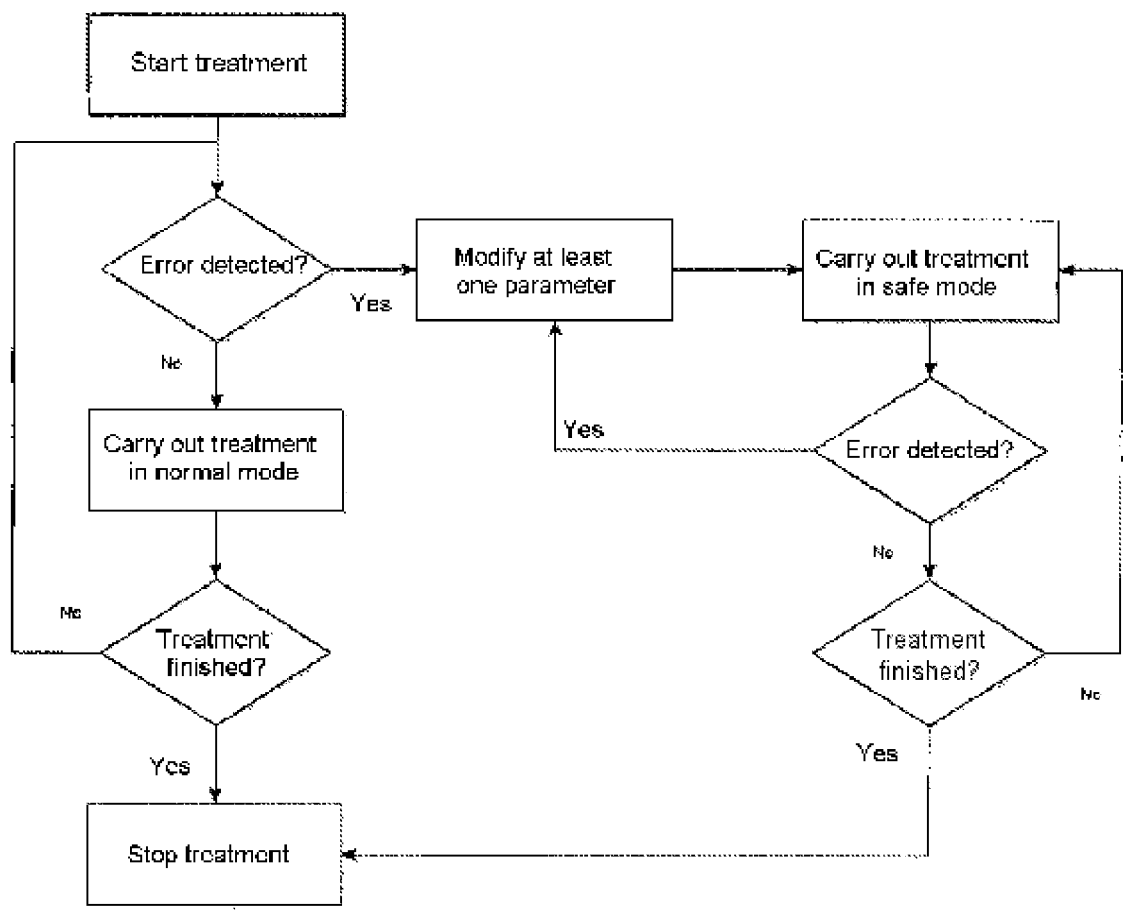
Figure 11B:
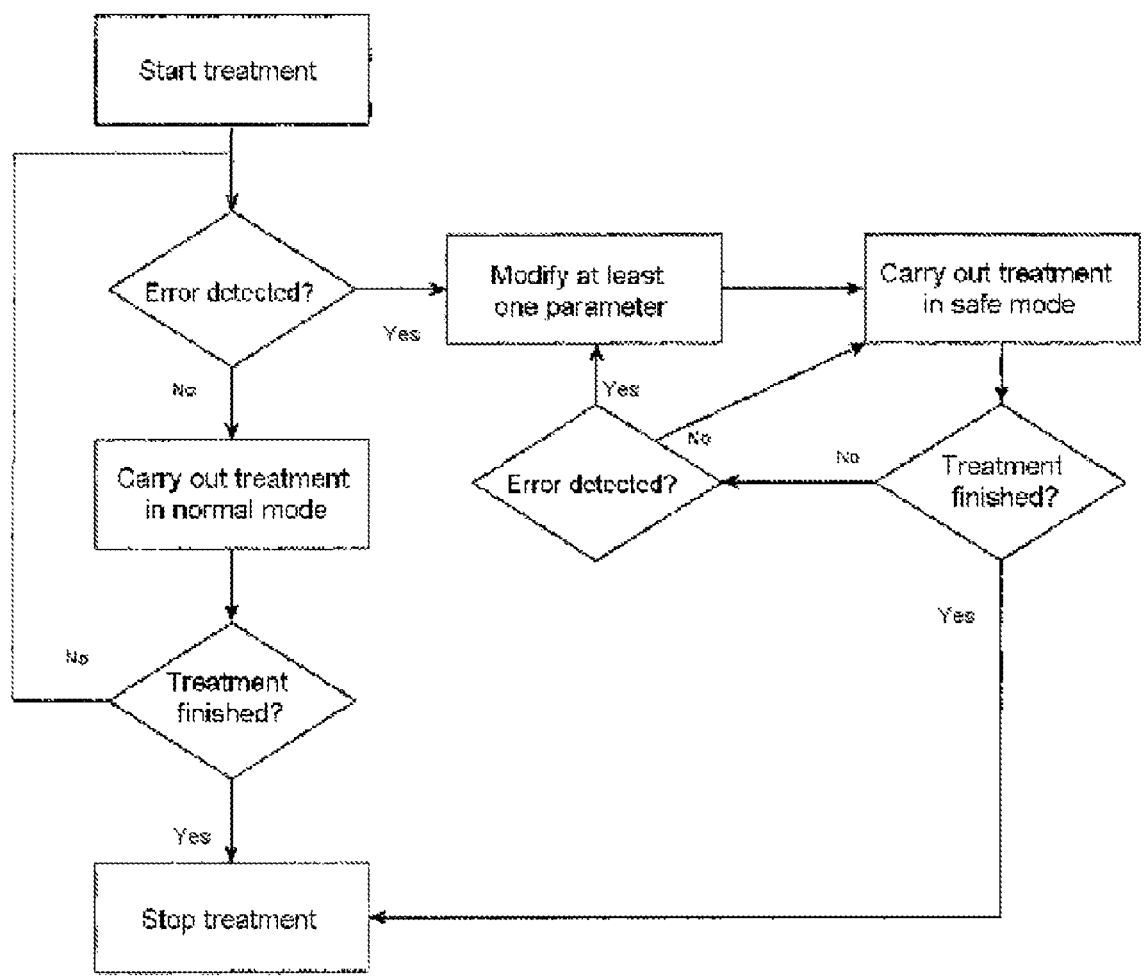

In one embodiment, the system is designed to operate as disclosed in FIGS. 10, 11a and 11b, reusing the concepts set out hereinabove.

Embodiments and Examples of Use

Figure 1:
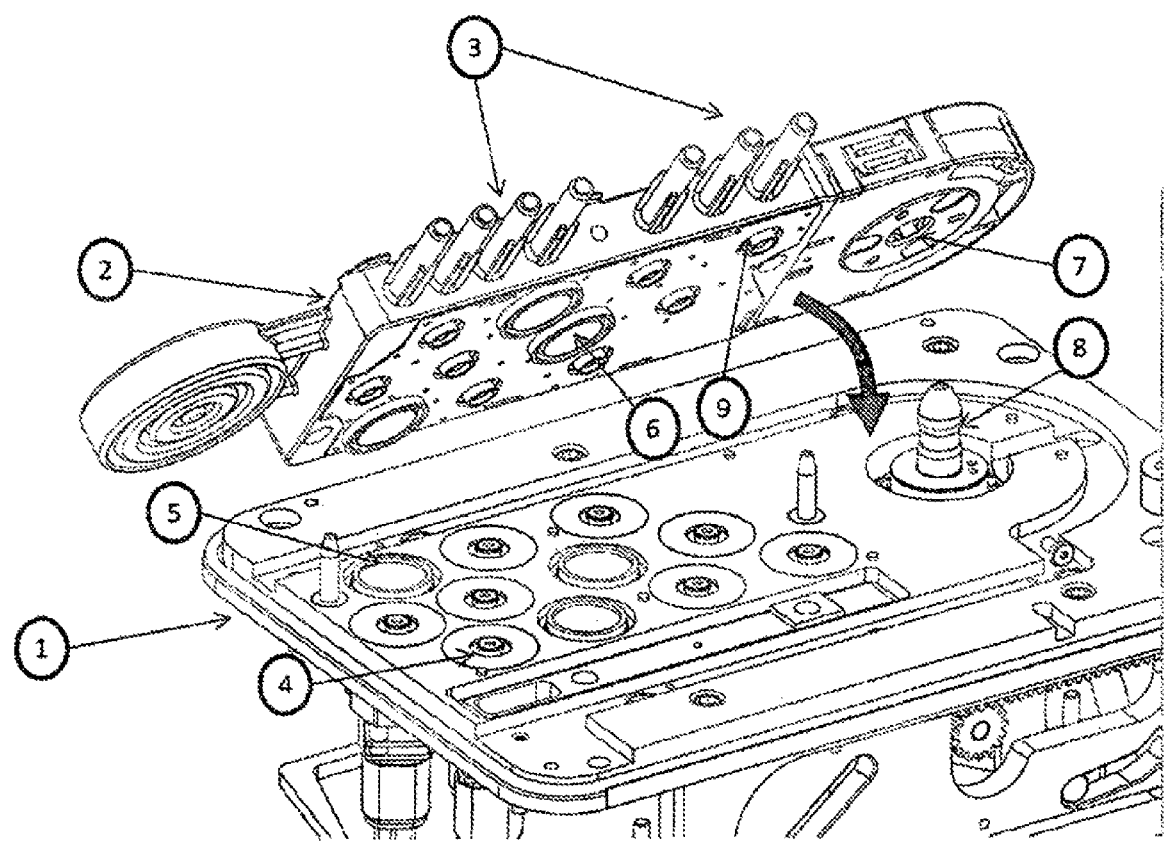
FIG. 1 illustrate the coupling between a cassette and a cycler.

For a better understanding of the operation, the description considers the example of a dialysis system as disclosed in FIG. 1. The dialysis system comprises a cycler (1) (here depicted without its housing), and a cassette (2). The cassette is a disposable element whereas the cycler is used several times with different cassettes. The cassette (2) comprises a pumping mechanism (7) which may be a peristaltic or some other type (pneumatic, etc.) of pump, fluid inlets and outlets (3), valves (9), regions for coupling with a sensor (5) of the cycler (1). The inlets and outlets (3) may be designed to be connected via a tube (not depicted) to: a dialysate reservoir (not depicted), a patient (not depicted), a heating system (not depicted) and/or a fill and/or drain system (not depicted). The cycler (1) comprises a processor (not depicted in FIG. 1), sensors (5), actuators (4, 8) designed to collaborate with the valves (9), the pumping mechanism (7) of the cassette. The cassette and the cycler are designed for perfect coupling of the sensors and actuators with the elements of the cassette. The cycler may also contain other sensors such as temperature sensors for measuring the temperature of the fluid or the ambient temperature, etc. If, for example, a sensor is defective or the cassette is defective or an element is present between the sensor and the cassette or between the cycler and the cassette, it may happen that the coupling between cassette and sensor is imperfect, giving rise to a drift in the data or giving rise to data that are completely erroneous. The membrane covering the flexible zone (6) may also be defective (noncompliant surface finish, deformation, etc.).

As in any fluid delivery system, the volume of fluid delivered or drained is an essential data item that needs to be controlled. In the prior art, mention is notably made of the danger of overfilling dialysate in the patient's peritoneum. It is thus essential to have control over this data, which is the result of the volume delivered and/or drained. According to the type of device, it may be crucial to check the absolute value of the volume of fluid delivered and of the volume drained, or simply to ensure a good control of the balance, namely good control over the difference between the volume delivered and the volume drained. These volumes may be estimated using the pump itself (piston pump, peristaltic pump, etc.) and/or using sensors arranged or not arranged on the fluid line. Now, this estimate may be dependent on a certain number of physical causes such as the state of wear of the pumping system, the pressure at the inlet and/or at the outlet of the pump, the temperature, the programmed fluidic path, etc. This makes accurately estimating these volumes difficult.

During a prior study, the effects of at least one of these parameters on the volume pumped is established by physical theory and/or numerical modeling and/or through characterization testing. This characterization testing may be carried out according to a test plan that is optimized to reduce the number of tests needed while at the same time covering the necessary range with sufficient precision. Such plans may be built on the basis of the "design of experiment" technique, using known methods (for example the Taguchi method) which may or may not include interaction between these causes. The physical values (for example the pressure of the fluid at the inlet of the pump) are themselves measured in the device by sensors. By measuring these physical values and with the corresponding effects previously established, the volume delivered by the pumping system can be corrected to improve its precision as disclosed in FIG. 7.

In general, each device comprises a determined number of sensors (often for cost and maintenance reasons). The system needs to operate with this limited number of sensors which means that the system has to operate with imperfect awareness of the environment and of certain factors. For example, the relative position of the patient and of the cycler is an important piece of information that will have an impact on the pressures of the fluid displaced in the cassette. In theory, the patient ought not to move during the treatment and the devices are not provided with sensors that are sufficiently precise to determine whether or not the patient moves during treatment. Now, if the patient changes position, for example if he rises by 20 cm with respect to the cycler, this will have a significant impact on the fluid pressure measurements and potentially also on the estimate of the displaced volumes. In other words, if the patient moves the cycler may detect that a variation in pressure has occurred, but does not necessarily know the cause for this (the origin of such a change in pressure may in actual fact have other causes such as, for example, the appearance of a restriction in the fluidic path. The cycler at best will notice this change but will have no means of discerning its origin). Thus, the cycler needs to operate to the best of its ability according to the given circumstances, according to the level of awareness of the status of the system and/or of the patient's environment. Thus, the system may have difficulty in assessing whether the observed change in the measurement is the result of a defect associated with the sensor or a movement of the patient.

For measurement reliability purposes it is common practice to have at least a level of redundancy in sensors (for example two independent sensors are used to measure the pressure at the inlet to the pumping device). These two sensors are regularly compared in order to detect any potential error with one of the sensors, originating for example from a drift in the measurement or degradation of the interface between the sensor and the environment that is to be measured. According to the prior art, as soon as one of the sensors is deemed to be defective, the system goes into alarm mode and the treatment is interrupted. The object of the invention in such a situation is to continue the treatment in a mode referred to as safe mode.

For greater clarity, the document sets out a system in which the means for calculating the volumes comprise a pressure sensor. However, these means may be other elements such as a volumetric chamber or a syringe plunger used for measuring volumes.

According to one embodiment set out in FIG. 8, the peritoneal dialysis device has two pressure sensors (31, 32) intended to measure the pressure at the inlet of a pumping system (30) (for example a peristaltic pump). According to the pressure measured, the system adapts the delivery rate of the pumping system (30) in order to take account of the variations in delivery rate as a function of said inlet pressure. The processor (34) analyzes the data measured by the pressure sensors (31, 32), estimates, as a function of at least these data, the quantity of fluid displaced by the pump. The processor is designed to adjust the operation of the pump (speed, rotational speed in the case of a peristaltic pump, delivery rate, operating time, etc.) accordingly in order to keep an effective delivery rate corresponding to the prescription.

In the event of a suspected failure of one of the pressure sensors, the system switches to safe mode. This mode of operation may reduce the volume of at least one fill phase in order to limit the filling of the peritoneal cavity by a percentage that corresponds, for example, to the possible maximum positive deviation of pumping or to a maximum tolerated deviation beyond which there could be a risk to the patient. By making this correction, the system ensures that the peritoneum is not overfilled (such overfilling for example representing a cardiovascular risk to the patient), even assuming that the sensor remaining operational should fail.

By way of example, in the event of failure of one of the two sensors (or assuming that one or both sensors is potentially defective), each filling of the peritoneal cavity in the next cycle will be reduced by 3% of the programmed volume. This percentage may be predefined according to the patient and/or according to the design of the system (the capacity of the pump, etc.). This percentage for example represents the risk of overfilling associated with this failure or the maximum excessive overfilling that could carry a risk to the patient. In this example, this may be a failure that is assumed because the discrepancy in measurement between the two sensors has crossed a certain threshold, leading to the assumption that at least one of the two sensors is defective or incorrectly coupled with the measurement zone (for example the membrane of the cassette).

During multiple fillings, this percentage may be adapted to take account of the cumulative effect of overfilling on each cycle (for example 8 cycles at 3% represents a maximum risk of 24% of overfill). Of course the percentage may be adapted to take account also of the lesser drainage due to the same fault on each cycle. Which may represent, for example 24%, for 8 filling cycles, which combine with the 24% of lower drainage giving a total of 48% overfill over 8 cycles, which is close to the tolerated limit.

These percentages may naturally differ greatly according to the filling and/or drainage conditions and the system will ideally best define the conditions for reducing the filling and/or increasing the drainage (in the case of partial drainage) in order to limit of risk of exceeding a 50% overfill (namely 150% of the peritoneal volume which is generally considered to be the acceptable limit). It is commonly conceded that 160% must under no circumstances be exceeded and that 180% carries a serious risk to the health of the patient. If the cumulative effect of various cycles carries a risk of causing these safety limits to be exceeded, it may be desirable during the treatment to carry out a full drainage cycle even though in the mode of normal operation the drainage of this cycle would not have been a complete drainage. Thus, by virtue of this complete drainage, the system ensures that the peritoneal cavity is drained almost completely and can therefore begin to cumulate the errors again from an empty belly. Thus, the system may carry out at least one complete drainage at fixed or variable cycle intervals or at intervals that may be dependent on the possible error percentage. This number may be set, for example, at 6 or 8 consecutive cycles.

As soon as a sensor detects an abnormal variation in the pressure, even though the system cannot truly know the cause of this, the processor may decide to modify the mode of operation in order to adapt to this variation. For example, before beginning the treatment, the system defines certain parameters such as the volume delivered, the delivery rate and/or the phases of exchange. The system will then operate in a mode of normal operation. If the pressures measured at the inlet of the pumping system lie within an acceptable pressure range, the mode of normal operation will be used throughout the treatment. However, if at some moment in the treatment the measurements drift suddenly or progressively, and then cross a certain threshold, then the system may switch to another mode of safe operation in order to adapt to these measurements. The system will define at least one new collection of parameters, for example a reduction in the delivery rate (because the pressure sensors have detected an increase in pressure, which could be due to the patient rising relative to the cycler). This mode of operation may be considered to be a mode of safe operation because it will potentially be less effective than the mode of normal operation. Here, the treatment will be slower because of the drop in flow rate. If the drift continues and crosses another threshold then the system may once again redefine a collection of new parameters.

In reality, the system does not know whether the patient has actually moved. This variation in pressure may be down to a number of causes. However, if this variation is due to the fact that the patient has, for example, risen by 20 cm, then the delivery rate needs to be lowered in order to avoid overfilling the patient's peritoneal cavity. It is for this reason that the system redefines these parameters even though the other systems of the prior art would have stopped the operation of the system. Each time the parameters are redefined, the system may also redefine the thresholds.

According to another embodiment, the safe mode takes account of possible errors in measuring the temperature of the fluid and, therefore, possible errors in the filling and/or drainage volume.

When the system is caused to switch to a mode of safe operation during a single treatment, the system may estimate that the cause of the problem was only temporary. In that case, the system may comprise a screen or an indicating means (colored LED, noise, etc.) to inform the patient that a problem has been detected during treatment. A memory may log these data so that the patient can transmit them to his or her doctor or with a view to logging machine errors. Ideally, the system will inform the patient that his or her treatment has been modified while in progress and that a certain percentage of the expected treatment will at least have been attained (for example 80%, which may quantify the therapeutic minimum obtained and cause the next treatments on subsequent days to be adapted, possibly accordingly).

If the problem should recur, which means to say occur repeatedly in different treatments, then the system may be designed to encourage the patient to intervene or request an intervention or the system may itself request intervention from the maintenance center. The screen may advise the patient to perform certain operations or invite him or her to contact the maintenance department.

As an example of operation of an embodiment allowing several adaptations, the pressure value measured at the pump inlet reaches a limit either because the patient has moved (with a sensor that is operational) or because the pressure sensor is drifting. In the latter instance, the sensor is defective and there is a risk of overfilling. To avoid overfilling, the delivery rate is reduced (which decreases the pressure at the inlet of the pump and therefore the risk of overfilling). This adaptation of the delivery rate corresponds to adaptation No. 1. With this new delivery rate, a new safety limit for the pressure measurement is calculated. If this new limit is reached, the delivery rate is reduced again, which corresponds to adaptation No. 2. The delivery rate can thus be reduced in succession n times (n adaptations) down to a delivery rate that no longer represents any risk (for example because the risk of overfilling is reduced below the safe limit of 120 to 150%). The consequence of this change in delivery rate will have an impact on the result of the treatment. Specifically, if the treatment is to be given over a determined length of time then all or part of the final cycle will not be able to be performed. In an extreme case, there may be a number of cycles that cannot be performed in order to comply with the predefined treatment duration. Thus, the result of the treatment will not be of such good quality as/will be less effective than the desired result. Thus, not all of the objectives of the treatment will be met. In other words, only some of the objectives will be met, in this instance at least the duration of the treatment. In another embodiment, it is the stasis duration that may be favored. Thus, the duration of stasis will be unchanged because it is predefined, but the total duration of the treatment will instead increase. The prescriber may determine in advantage which objectives cannot be modified or which are to be prioritized in the event of a problem. Thus, he or she may predefine the parameters that cannot be changed by the processor when switching to a mode of safe operation.

In instances in which the system comprises two redundant sensors, the method or methods described hereinabove are particularly suitable when one or both sensors are defective or when the cassettes is incorrectly installed in the cycler or when the pressure sensor or sensors are incorrectly coupled to the cassette.

Example of operation of an embodiment allowing complete drainage, a fault is detected which, in the worst case scenario, represents a risk of overdosing of the pumping device by 6%. Thus, in theory, on each cycle, 6% of volume is added to the volume already present, which represents a volume in the peritoneum of 106% in the first cycle, 112% in the second cycle, etc. In this example, there are two possible protective measures. The first is to reduce the volume injected in the filling phases by 3%. The second is to impose a complete drainage phase at the end of 8 cycles. On balance, the cumulative errors over 8 cycles represent a maximum volume in the peritoneum of 100%+8×3%, namely 124%, which is an acceptable volume.

Possible Methods:

The document further discloses a method for controlling a medical system according to a defined treatment in order to achieve a collection of objectives, the method comprising:
  providing a dialysis system which comprises:
    a processor designed to control the medical system according to at least two modes of operation:
      a mode of normal operation determined by a first collection of parameters making it possible to achieve substantially all of the objectives defined by the treatment
      a mode of safe operation determined by a second collection of parameters that does not allow all of the objectives defined by the treatment to be achieved but that does allow the treatment to be performed substantially,
    a sensor designed to send signals to the processor,
  determining at least one condition of operation,
  receiving and analyzing the signals from the sensor,
  automatically selecting the mode of normal operation or the mode of safe operation according to the signal analysis and/or said at least one condition of operation,
  controlling the medical system according to the mode of operation selected.

The system described hereinabove may be designed to operate according to several modes of safe operation. Also, the processor may switch from one mode of safe operation to another mode of safe operation progressively.

According to one embodiment, the medical system comprises a pump controlled by the processor and designed to displace a medical fluid. The medical system may, for example, be a dialysis system.

Optionally, the method may comprise the following step: adapting at least one condition of operation according to the mode of operation selected.

According to one embodiment, the parameter may be: the duration of the treatment, a volume of medical fluid displaced by the pump, a volume of medical fluid used, the temperature or the pressure of the displaced fluid or the delivery rate of the pump. If the medical device comprises a pump, then the mode of safe operation may be characterized by a pump delivery rate that is not as high as in the mode of normal operation.

For preference, the processor during treatment may switch from one mode of operation to another defined mode of operation according to the signal analysis and/or to said at least one condition of operation.

If the treatment is a peritoneal dialysis then the dialysis system may be designed to perform several successive cycles comprising an injection phase in which the system injects the medical fluid into the peritoneum of the patient, a stasis phase in which the medical fluid remains in the patient's peritoneum for a determined length of time, and a drainage phase in which the pump removes the fluid from the patient's peritoneum. In that case, the parameter(s) may be: the duration of each stasis phase, the total volume of fluid injected into and/or removed from the peritoneum, the volume of fluid injected into the peritoneum during an injection phase, the volume of fluid removed from the peritoneum during a drainage phase, the number of cycles, the duration of the phases or the delivery rate of the pump in the injection and/or drainage phase. Furthermore, during a mode of safe operation, the processor may be designed to command a complete forced drainage of the peritoneum at least once before the end of the treatment. Optionally, the processor may be designed to perform several forced drainages at defined intervals.

According to one embodiment, the mode of safe operation may be designed to decrease the risk of overfilling the patient's peritoneum during the treatment. Further, the medical device may be designed to estimate the risk of overfilling or underfilling the patient's peritoneum.

For preference, one condition of operation is: the status of the sensor, a drift in the sensor measurement, the crossing of a threshold or the leaving of a predefined domain, or a discrepancy in the measurement against another sensor. The sensor may be a pressure sensor or a temperature sensor.

The document discloses another method designed to control a dialysis apparatus. This other method may comprise the following steps:
  observing at least one parameter relating to the dialysis
  determining a first acceptable range of values for said parameter.

For preference, the switchover from one mode of operation to a first mode of safe operation if the data of said at least one parameter are outside said first range of acceptable values. The observed parameter may be the volume of dialysate displaced to and/or from a patient's peritoneum.
  The method may also comprise:
  the following additional steps:
    determining a second range of acceptable values for said parameter
    switching from the first mode of downgraded operation to a second mode of safe operation if the data of said at least one parameter are outside said second range of acceptable values.
  And/or the following additional steps:
    determining an nth range of acceptable values for said parameter
    switching from the n−1th mode of downgraded operation to an nth mode of safe operation if the data of said at least parameter are outside said nth range of acceptable values.

Other Possible Embodiments

The document discloses a system for medical use which may comprise a pump, means for estimating a volume of fluid displaced by the pump, means for operating said pump according to the objectives defined for the treatment; in which said pump is designed to deliver a fluid to a patient or to remove a fluid from a patient. The operating means may determine a mode of operation of the pump as a function of data sent by the means of estimating displaced volume. Furthermore, at least one mode of operation may be a safe mode allowing the system to continue the treatment in order to get close to at least one of the objectives defined for the treatment in the event of at least part of the operating and/or estimating means being potentially defective, while at the same time limiting the risks to the patient.

The operating means may change the mode of operation without the intervention of the patient or of the care personnel. The treatment may correspond to that of a peritoneal dialysis and may comprise at least two cycles of fill and drain phases.

Optionally, during a safe mode, the operating means may reduce the volume of fluid displaced during at least one fill phase and/or increase the volume of fluid displaced during at least one drain phase.

At least one of the objectives may be the treatment time, the quantity of ultrafiltrate removed, the volume of fluid delivered to the patient's peritoneum and/or the volume of liquid removed from the patient's peritoneum, and/or the total dialysis time performed. The means of estimating the displaced volumes may comprise one or more pressure sensors or volumetric chambers. The means of estimating the displaced volumes may comprise one or more temperature and/or viscosity sensors, or calibration means. In such a case or cases, the estimating means may be redundant and at least one of the two means may be deemed to be potentially defective, thus leading to the safe mode being activated. The redundant estimation means may deviate from one another by a certain amount at least. The filling phase of each cycle in safe mode may be reduced by at least 1% of the prescribed volume. The drainage phase of each cycle in safe mode may be increased by at least 1% of the prescribed volume, if the prescribed drainage is not a total drainage. The most complete possible drainage may be imposed during at least one drain phase if the potential overfilling of the peritoneal cavity as a result of the cumulative effect of the various preceding cycles crosses a threshold of between 120 and 180%.

According to one embodiment, the automated dialysis apparatus is designed to perform peritoneal dialysis on a patient and may comprise a pump operated by a controller and designed to displace at least a first defined volume of dialysate from dialysate supply means into the peritoneal cavity of the patient during a fill phase and to remove at least a first defined volume of dialysate from the patient's peritoneal cavity during a drain phase. The apparatus may further comprise a sensor connected to the controller and designed to estimate the volumes of dialysate displaced during at least one of these two phases.

For preference, the apparatus comprises at least two modes of operation one of them being a mode of operation that allows all the defined objectives to be achieved and at least one other being a mode of safe operation designed to come close to at least one of said defined objectives without ever achieving it, while at the same time ensuring patient safety. The mode of operation may be determined by the controller without the intervention of the patient or of the care personnel, for example as a function of the estimate of the volumes displaced.

For preference, the mode of safe operation may be actuated by the controller as soon as an error in the estimation of the volumes is possible or detected. The mode of safe operation may be determined by the controller as soon as the data from the sensor cross a certain measurement threshold or exhibit a certain difference with respect to the expected measurement. The mode of safe operation may be designed to reduce the delivery rate of the pump or the duration of the treatment or at least a volume of dialysate delivered during at least one fill phase.

According to one embodiment, the apparatus may comprise several successive safe modes which allow treatment to be continued but which increasingly diverge from at least one of the defined objectives. The controller may select one of the safe modes according to the measurements from at least one of the sensors. The controller may progressively modify its mode of operation until the measurements from the sensor fall within a predefined range.

According to one embodiment, the peritoneal dialysis system may comprise a liquid pump, means for operating said pump. Where the pump is designed to deliver or remove a liquid to or from the peritoneal cavity of a patient and the system may be configured to operate according to at least one of the following two modes of operation:
- a first mode of operation referred to as normal defining a first collection of parameters intended to achieve a given treatment effectiveness
- a second mode of operation referred to as safe defining a second collection of parameters intended to achieve: minimum effectiveness of the treatment, and/or effectiveness lower than the effectiveness of the first embodiment, while ensuring patient safety during the treatment.

In another embodiment, the system may be configured to operate according to at least one of the following two modes of operation:
- a first mode of operation referred to as normal adhering to the parameters defined by a given prescription
- a second mode of operation referred to as safe which does not adhere to at least one of the parameters defined by said prescription but which guarantees patient safety until the end of the programmed treatment.

According to one possible embodiment, the automated dialysis apparatus is designed to perform peritoneal dialysis on a patient in accordance with a collection of parameters defined by a given prescription guaranteeing a certain treatment effectiveness. The apparatus may comprise a liquid pump, means of operating said pump according to parameters defined by a given prescription. Where the pump is designed to deliver or remove a liquid into or from the peritoneal cavity of a patient and the apparatus is configured to modify at least one of said parameters so as to perform substantially the entirety of the treatment while at the same time guaranteeing patient safety. However, the new parameters might not allow the expected effectiveness to be achieved, in response to a suspected at least partial deficiency with an element (for example a sensor, a pump) to operate said dialysis apparatus correctly.

The invention claimed is:

1. A dialysis system for performing a peritoneal dialysis by a defined treatment of a patient, the dialysis system comprising:
   a processor configured to control the dialysis system to deliver a dialysate solution with a plurality of delivery cycles to a peritoneum of the patient during the defined treatment;
   a pressure sensor for measuring a pressure of the dialysate solution in a fluidic pathway and providing a pressure signal to the processor; and
   a pump controlled by the processor and configured to displace the dialysate solution through the fluidic pathway to the patient,
   wherein the processor is configured to,
      control the pump to deliver the dialysate solution at a fluid delivery rate to the patient;
      estimate a displaced volume of the dialysate solution delivered to the peritoneum based on measurements of the pressure sensor;
      analyze the pressure signal from the pressure sensor of the dialysis system to determine a variation of the pressure of the dialysate solution from a threshold value caused by a failure condition of the dialysis system;
      control the pump to reduce the fluid delivery rate of the dialysate solution to a reduced safe fluid delivery rate such that a cumulated error during the plurality of delivery cycles caused by of the variation of the pressure does not cause an overfilling the peritoneum by the delivered dialysate solution; and
      determine a new threshold value for the analyzing the pressure signal based on the reduced safe fluid delivery rate.

2. The dialysis system as claimed in claim 1, wherein the processor is configured to determine a set of parameters of the operation of the dialysis system, the set of parameters including at least one of a duration of the defined treatment, a volume of the medical fluid displaced by the pump, a volume of the medical fluid used, a temperature of the displaced fluid, a pressure of the displaced fluid, and a delivery rate of the pump.

3. The dialysis system as claimed in claim 2, wherein the set of parameters further including a duration the stasis phase, a total volume of the medical fluid injected into the peritoneum, a total volume of the medical fluid removed from the peritoneum, a volume of the medical fluid injected into the peritoneum during an injection phase, the volume of fluid removed from the peritoneum during a drainage phase, the number of cycles, a duration of the injection phase, a duration of the drainage phase, a delivery rate of the pump in the injection phase, and a delivery rate of the pump in the drainage phase.

4. The dialysis system as claimed in claim 1,
   wherein the processor instructs the dialysis system to perform several successive cycles including,
      an injection phase in which the dialysis system injects the medical fluid into the peritoneum of a patient,
      a stasis phase in which the medical fluid remains in the peritoneum of the patient for a determined length of time, and
      a drainage phase in which the pump removes the medical fluid from the peritoneum of the patient.

5. The dialysis system as claimed in claim 4, wherein the processor is further configured to estimate a risk of at least one of overfilling and underfilling the peritoneum of the patient based on the pressure signal.

6. The dialysis system as claimed in claim 4, wherein the processor is further configured to instruct complete forced drainage of the peritoneum at least once before an end of the defined treatment.

7. The dialysis system as claimed in claim 4, wherein the processor is further configured to perform several forced drainages at defined intervals.

8. The dialysis system as claimed in claim 4, wherein when the processor controls the pump to reduce the fluid delivery rate to the reduced safe fluid delivery rate, the processor further is further configured to reduce the number of cycles of the treatment as compared to a number of cycles when the pump is operated at the fluid delivery rate.

9. The dialysis system as claimed in claim 1, wherein the reduced safe fluid delivery rate includes a plurality of reduced safe fluid delivery rates.

10. The dialysis system as claimed in claim 9, wherein the processor is configured to switch from one reduced safe fluid delivery rate to another reduced safe fluid delivery rate mode of safe operation among the plurality of reduced safe fluid delivery rates.

11. The dialysis system as claimed in claim 1, wherein the processor is further configured to determine a condition of the operation of the dialysis system, the condition of operation includes at least one of a status of the pressure sensor, a drift in a measurement of the pressure sensor, a crossing of a threshold in a measurement of the pressure sensor, a leaving of a predefined range in a measurement of the pressure sensor, and a discrepancy in a measurement against another pressure sensor.

12. The dialysis system as claimed in claim 1, further comprising a temperature sensor operatively connected to the dialysis system.

13. The dialysis system as claimed in claim 12, wherein the processor is further configured to estimate the displaced volume of the dialysate solution delivered to the peritoneum based on measurements of the temperature sensor.

14. The dialysis system as claimed in claim 1, further comprising:
an additional pressure sensor that measures a pressure of the dialysate solution in the fluidic pathway at a different location as compared to the pressure sensor,
wherein the processor is further configured to analyze the pressure of the additional pressure sensor, and is configured to control the pump to provide the reduced safe fluid delivery rate when the processor has determined that a difference between the two measured pressures is above a defined threshold.

15. The dialysis system as claimed in claim 1, wherein the processor is configured to determine a displaced volume of the dialysate per unit time.

16. The dialysis system as claimed in claim 15, wherein when the processor controls the pump at the reduced safe fluid delivery rate, the processor is further configured to reduce an amount of the displaced volume of dialysate by a percentage value as compared to the determined displaced volume.

17. The dialysis system as claimed in claim 16, wherein the reduced amount of the displaced volume is applied with a next injection phase.

18. The dialysis system as claimed in claim 1, wherein when the processor controls the pump to reduce the reduced safe fluid delivery rate, no alarm is generated to alert the patient.

19. The dialysis system as claimed in claim 1, wherein the pressure sensor is configured to measure the pressure of the fluidic pathway at an inlet of the pump.

20. The dialysis system as claimed in claim 1, wherein the processor is further configured to automatically apply another reduced safe fluid delivery rate after the processor has determined that the reduced safe fluid delivery rate is insufficient to prevent the overfilling of the peritoneum, the another reduces safe fluid deliver rate having a fluid delivery rate is further reduced as compared to the reduced safe fluid delivery rate.

21. The dialysis system as claimed in claim 1, wherein when the reduced safe fluid delivery rate is selected, a new set of parameters are used to increase the total duration of a treatment as compared to a total duration of the defined treatment with the fluid delivery rate.

22. The dialysis system as claimed in claim 1, wherein the pressure sensor is arranged upstream to the pump such that the pump is located between the pressure sensor and the patient when the pump displaces the dialysate solution to the peritoneum of the patient.

23. The dialysis system as claimed in claim 1, further comprising:
a redundant pressure sensor configured to measure the pressure of the dialysate solution in the fluid pathway located in proximity to the pressure sensor.

24. A dialysis system for performing a dialysis treatment to a patient, the dialysis system comprising:
a fluidic pathway in fluid communication with the patient peritoneum;
a pump configured to displace a dialysate solution through the fluidic pathway to or from the patient;
an inlet pressure sensor for measuring a pressure of the dialysate solution in the fluidic pathway, the inlet pressure sensor arranged upstream to the pump such that the pump is located between the pressure sensor and the patient when the pump displaces the dialysate solution to the patient peritoneum; and
a processor configured to control pump according to a determined dialysis treatment and to receive a pressure signal from the inlet pressure sensor, the processor being further configured to:
control the pump to displace the dialysate solution at a first flow rate;
estimate a displaced volume of the dialysate solution delivered to the peritoneum based on measurements of the inlet pressure sensor;
analyze the pressure signal from the inlet pressure sensor of the dialysis system to determine a variation of the pressure of the dialysate solution from a threshold value caused by a failure condition of the dialysis system; and
control the pump to displace the dialysate solution at a reduced second flow rate and determine a new threshold value based on the reduced second flow rate when the variation of pressure from the threshold value has been determined in the analyzing.

25. The dialysis system as claimed in claim 24, wherein the processor is further configured to estimate a risk of overfilling or underfilling the peritoneum of the patient based on the pressure signal.

26. The dialysis system as claimed in claim 24, further comprising:
a temperature sensor operatively connected to the dialysis system.

27. The dialysis system as claimed in claim 26, wherein the processor is further configured to estimate a displaced volume of the dialysate solution delivered to the peritoneum of the patient based on measurements of the temperature sensor.

28. The dialysis system as claimed in claim 24, further comprising:
an additional pressure sensor that measures a pressure of the dialysate solution in the fluidic pathway,
wherein the processor is further configured to analyze the pressure of the additional pressure sensor, and is configured to control the pump to deliver the reduced second flow rate when the processor has determined that a difference between the two measured pressures is above a defined threshold.

29. The dialysis system as claimed in claim 24, wherein when the processor controls the pump at the reduced second flow rate, the processor is further configured to reduce an amount of the displaced volume of dialysate by a percentage value as compared to a determined displaced volume when the processor controls the pump at the first flow rate.

30. The dialysis system as claimed in claim 29, wherein the reduced amount of the displaced volume is applied with a next injection phase.

31. The dialysis system as claimed in claim 24, wherein the dialysis treatment comprises a succession of cycles dc cycic including at least one of a fill phase and a drain phase.

32. The dialysis system as claimed in claim 31, wherein the processor is further configured to instruct complete forced drainage of the peritoneum at least once before an end of the defined treatment.

33. The dialysis system as claimed in claim 31, wherein when the processor controls the pump at the reduced second flow rate, the processor further configured to reduce the number of cycle of the treatment as compared to a number of cycle when the pump pumps at the first flow rate.

34. A dialysis system for performing a dialysis treatment to a patient, the dialysis system comprising:
a fluidic pathway in fluid communication with a peritoneum of the patient;
a pump configured to displace a dialysate solution through the fluidic pathway to or from the patient;
an inlet pressure sensor for measuring a pressure of the dialysate solution in the fluidic pathway; and
a processor configured to control pump according to a determined dialysis treatment, to receive a pressure signal from the inlet pressure sensor, and to estimate a displaced volume of the dialysate solution delivered to the peritoneum based on measurements of the inlet pressure sensor;
wherein the processor is further configured to,
control the pump to displace the dialysate solution at a first flow rate;
determine a first threshold value based on the first flow rate;
analyze the pressure signal from the inlet pressure sensor of the dialysis system to determine a variation of the pressure of the dialysate solution from the first threshold value;
control the pump to displace the dialysate solution at a reduced second flow rate when a variation of the pressure from a first threshold value has been determined by the analyzing;
determine a second threshold value based on the reduced second flow rate;
analyze the pressure signal from the inlet pressure sensor of the dialysis system to determine a variation of the pressure of the dialysate solution from the second threshold value; and
control the pump to displace the dialysate solution at a further reduced third flow rate when a variation of the pressure from the second threshold value has been determined by the analyzing.

35. The dialysis system as claimed in claim 34, wherein the pressure sensor is arranged upstream to the pump such that the pump is located between the pressure sensor and the patient when the pump displaces the dialysate solution to the peritoneum.

36. The dialysis system as claimed in claim 34, wherein the processor is further configured to estimate a risk of an overfilling or underfilling the peritoneum of the patient based on the pressure signal.

37. The dialysis system as claimed in claim 34, further comprising:
a temperature sensor operatively connected to the dialysis system.

38. The dialysis system as claimed in claim 37, wherein the processor is further configured to estimate a displaced volume of the dialysate solution delivered to the peritoneum based on measurements of the temperature sensor.

39. The dialysis system as claimed in claim 34, further comprising:
an additional pressure sensor that measures a pressure of the dialysate solution in the fluidic pathway,
wherein the processor is further configured to analyze the pressure of the additional pressure sensor, and is configured to control the pump to deliver the reduced second flow rate when the processor has determined that a difference between the two measured pressures is above a defined threshold.

40. The dialysis system as claimed in claim 34, wherein when the processor controls the pump at the reduced second flow rate, the processor is further configured to reduce an amount of the displaced volume of dialysate by a percentage value as compared to a determined displaced volume when the processor controls the pump at the first flow rate.

41. The dialysis system as claimed in claim 40, wherein the reduced amount of the displaced volume is applied with a next injection phase.

42. The dialysis system as claimed in claim 34, wherein the dialysis treatment includes a succession of cycles including at least one of a fill phase and a drain phase.

43. The dialysis system as claimed in claim 42, wherein the processor is further configured to instruct complete forced drainage of the peritoneum at least once before an end of the defined treatment.

44. The dialysis system as claimed in claim 42, wherein when the processor controls the pump at the reduced second flow rate, the processor further configured to reduce the number of cycle of the treatment as compared to a number of cycle when the pump pumps at the first flow rate.

* * * * *